(12) United States Patent
Swenson et al.

(10) Patent No.: US 11,219,771 B2
(45) Date of Patent: Jan. 11, 2022

(54) INTRA-CARDIAC COMMUNICATIONS USING ULTRASOUND TO PROVIDE DIRECT TIMING INFORMATION WITHOUT ELECTRICAL INTERFERENCES

(71) Applicant: BIOTRONIK SE & CO. KG, Berlin (DE)

(72) Inventors: Kurt Swenson, Dayton, OR (US); Ramprasad Vijayagopal, Sugar Land, TX (US); Karl-Heinz Freiberg, Woodburn, OR (US)

(73) Assignee: BIOTRONIK SE & Co. KG, Berlin (DE)

(*) Notice: Subject to any disclaimer, the term of this patent is extended or adjusted under 35 U.S.C. 154(b) by 47 days.

(21) Appl. No.: 16/825,668

(22) Filed: Mar. 20, 2020

(65) Prior Publication Data
US 2020/0324128 A1  Oct. 15, 2020

Related U.S. Application Data

(60) Provisional application No. 62/832,888, filed on Apr. 12, 2019.

(51) Int. Cl.
*A61N 1/372* (2006.01)
*A61N 1/375* (2006.01)
*A61N 1/368* (2006.01)
*H04B 11/00* (2006.01)

(52) U.S. Cl.
CPC ......... *A61N 1/37217* (2013.01); *A61N 1/368* (2013.01); *A61N 1/37512* (2017.08); *H04B 11/00* (2013.01)

(58) Field of Classification Search
CPC ........... A61N 1/37217; A61N 1/37512; A61N 1/368; A61N 1/37252; A61N 1/3756; A61N 1/37288; H04B 11/00; A61B 5/283; A61B 5/4836; A61B 5/0028; A61B 5/0031
See application file for complete search history.

(56) References Cited

U.S. PATENT DOCUMENTS

| 9,623,251 B2 | 4/2017 | Stahmann | |
| 2004/0204744 A1 | 10/2004 | Penner et al. | |
| 2006/0009818 A1* | 1/2006 | Von Arx | A61B 5/0028 607/60 |
| 2007/0093875 A1* | 4/2007 | Chavan | A61N 1/3605 607/46 |
| 2010/0249882 A1* | 9/2010 | Houben | A61N 1/37217 607/60 |
| 2011/0004075 A1* | 1/2011 | Stahmann | A61B 5/283 600/301 |

(Continued)

FOREIGN PATENT DOCUMENTS

| WO | 2007050657 A1 | 5/2007 |
| WO | 2018229716 A1 | 12/2018 |

*Primary Examiner* — Catherine M Voorhees
(74) *Attorney, Agent, or Firm* — Laurence A. Greenberg; Werner H. Sterner; Ralph E. Locher

(57) ABSTRACT

A medical system contains a first implantable device and a second implantable device. Each implantable device contains a communication unit configured to transmit an ultrasonic signal to the communication unit of another implantable device of the medical system. The first implantable device is configured to periodically transmit a broadcast message to at least the second implantable device using the communication unit of the first implantable device.

13 Claims, 2 Drawing Sheets

(56) References Cited

U.S. PATENT DOCUMENTS

| | | |
|---|---|---|
| 2015/0224320 A1 | 8/2015 | Stahmann |
| 2015/0335894 A1 | 11/2015 | Bornzin et al. |
| 2016/0121128 A1* | 5/2016 | Fishler ............... A61N 1/37288 |
| | | 607/14 |
| 2018/0168463 A1* | 6/2018 | Morris ................. A61B 5/4836 |

* cited by examiner

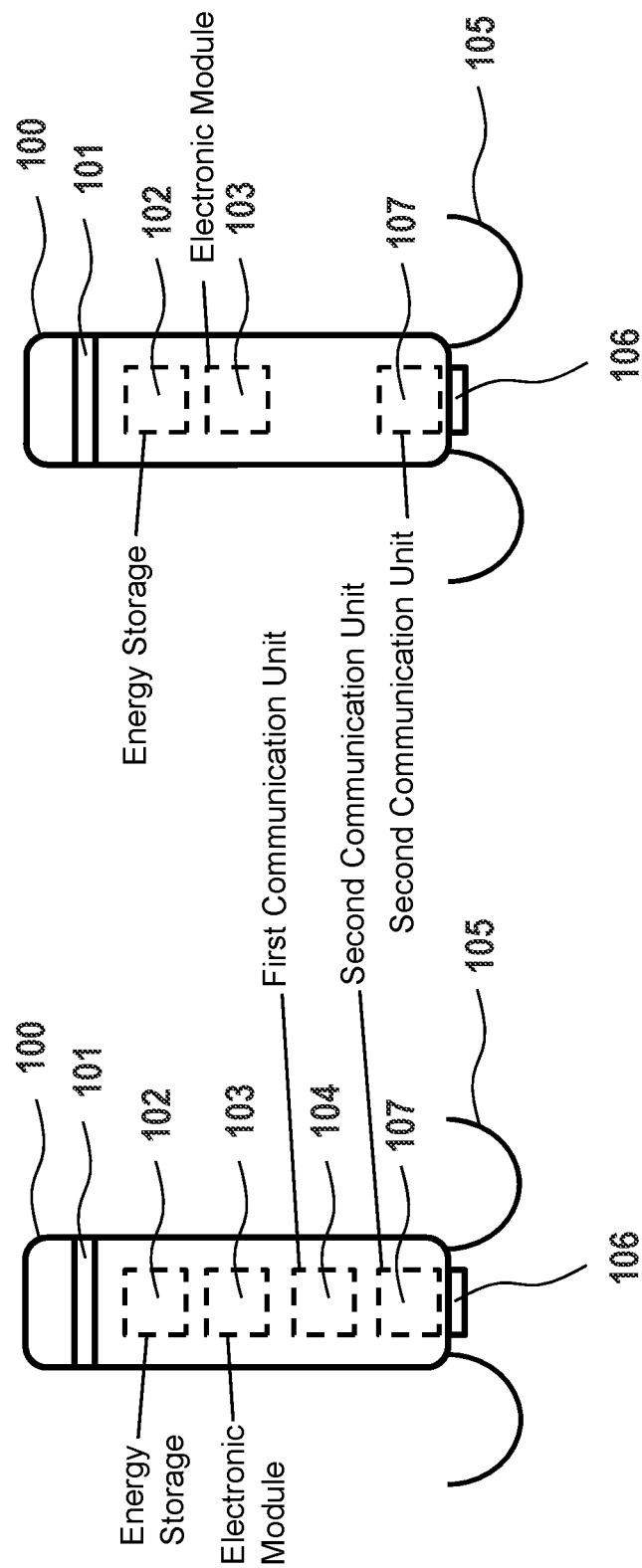

INTRA-CARDIAC COMMUNICATIONS USING ULTRASOUND TO PROVIDE DIRECT TIMING INFORMATION WITHOUT ELECTRICAL INTERFERENCES

CROSS-REFERENCE TO RELATED APPLICATION

This application claims the benefit, under 35 U.S.C. § 119(e), of provisional patent application No. 62/832,888 filed Apr. 12, 2019; the prior application is herewith incorporated by reference in its entirety.

BACKGROUND OF THE INVENTION

Field of the Invention

The present invention relates to a medical system, particularly to a pacemaker system comprising at least a first and a second implantable leadless pacemaker.

A leadless pacemaker system requires at least one implantable leadless pacemaker for each chamber in which pacing is to occur. Part of the job of a two (or even three) chamber pacemaker system is to correct broken intrinsic timing connections between the chambers. Another part is to control the timing of the complete cardiac cycle in a manner that meets the cardiac demands of the patient by controlling the rate at which pacing occurs.

Because leadless pacemakers in such a system do not have wires to carry information from one chamber to another, some form of communications between the chambers is required to allow the rate and timing synchronization necessary to meet these requirements.

Communications of event timing information is time critical. An event in one chamber can immediately trigger a response behavior in another chamber. Communication of other kinds of information may not be as time critical. For example, if a pacing rate is calculated in one chamber, it may be useful to share that information with the leadless pacemaker in another chamber, but the timing of the information exchange does not convey any necessary additional information. Another kind of data transfer may be done to allow one leadless pacemaker to configure the behavior in another leadless pacemaker in order to provide a coordinated system behavior. The configuration information is typically not time critical although there may be a need to use a synchronization signal to allow both devices to switch configurations at the same time.

Particularly, U.S. patent publication No. US 2015/0224320 AI discloses a leadless pacemaker system comprising a first leadless cardiac pacemaker implantable at a first heart site, and a second leadless cardiac pacemaker implantable at a second heart site, wherein the first pacemaker is configured to communicate information related to a cardiac event that is sensed by the first pacemaker at the first heart site to the second pacemaker.

Furthermore, U.S. Pat. No. 9,623,251 B2 describes a leadless cardiac pacemaker system comprising a first leadless cardiac pacemaker configured to be implantable at a ventricular site, and a second leadless cardiac pacemaker configured to be implantable at an atrial site. The second pacemaker is configured to sense atrial contractions, and the first pacemaker and the second pacemaker are configured to be communicatively coupled such that the second pacemaker can communicate sensed atrial contractions to the first pacemaker.

Further, U.S. patent publication No. US 2015/0335894 A1 discloses a distributed leadless implantable system, comprising a first and second leadless implantable medical device configured to be implanted entirely within first and second chambers of the heart. Each of the first and second device comprising: a housing having a proximal end configured to engage local tissue of interest in a local chamber; electrodes located along the housing; cardiac sensing circuitry configured to detect intrinsic and paced cardiac events occurring in a near field associated with the local chamber; and a controller configured to analyze the intrinsic and paced events and, based thereon, produce a trigger pulse at the electrodes when an event of interest occurs in the local chamber. A pulse sensing circuitry is provided and configured to detect at least one of a paced event or a trigger pulse occurring in a far field, where the paced event or trigger pulse originates in a remote chamber that differs from the corresponding local chamber. The trigger pulse has a predetermined pattern configured to indicate that an event of interest has occurred in the remote chamber. The controller is configured to recognize the at least one of the paced event or trigger pulse to indicate an occurrence of the event of interest in the remote chamber and, in response thereto, initiate a related action in the local chamber.

Typically, in two implant systems such as the ones described above, some of the information exchange in the system is time critical, and in some cases directly triggered by intrinsic cardiac events, so that there is the potential for messages to occur concurrently, resulting in collisions in which some information may be lost.

Particularly, when the pathway for information exchange is via modulated electrical pulses conducted in the heart tissue, the intrinsic electrical activity in the tissue can interfere with the data transmission. A typical solution would be to send data only during refractory periods, but this prevents sending time critical event flags.

SUMMARY OF THE INVENTION

Based on the above, it is an objective of the present invention to provide a system that is capable of using a communication pathway that does not compete with electrical activity within the heart tissue.

Furthermore, it is desirable to categorize information transfer between devices in different heart chambers into time critical and non-time critical messages. Furthermore, it is desirable to provide a collision avoidance mechanism for sending non-time critical information.

In one aspect, a medical system is disclosed, comprising at least a first implantable device and a second implantable device. Each implantable device comprises a communication unit configured to transmit an ultrasonic signal (e.g. a modulated ultrasonic pressure wave) to the communication unit of the other implantable device(s) of the medical system.

According to an embodiment of the medical system, the respective communication unit comprises a piezoelectric transducer.

Furthermore, according to an embodiment of the medical system, the respective communication unit is configured to receive an ultrasonic signal (e.g. a modulated ultrasonic pressure wave) from the other communication unit(s).

Particularly, the piezoelectric-based ultrasonic transducer in each implantable device can be electrically induced to create modulated pressure waves that can carry information to the other device(s). The same transducer would generate electrical signals proportional in response to the incoming modulated pressure waves. Particularly, these signals can be filtered and amplified before being demodulated to recover the transmitted information.

Furthermore, according to an embodiment, the respective transducer is isolated from the biological tissue by being enclosed within a housing that is also used to isolate a battery and/or electronics of the respective implantable device (e.g. an implantable leadless pacemaker) from the tissue of the patient. Particularly, the mechanical interface between the respective transducer and the housing is configured to allow mechanical coupling between pressure waves in the biological environment and the transducer.

Furthermore, according to an embodiment of the medical system, the first implantable device is a first implantable leadless pacemaker that is configured to be implanted into an atrium (e.g. right atrium) of the heart of a patient, and wherein the second implantable device is a second implantable leadless pacemaker that is configured to be implanted into a ventricle (e.g. on the same side as the atrium, e.g. right ventricle) of the heart of the patient.

Particularly, the respective implantable leadless pacemaker comprises a pacing electrode arranged on a housing of the pacemaker, wherein the housing is configured to be anchored to the heart wall in the atrium or ventricle.

Implantable devices for implantation into the atrium of the heart of a patient need to be very small and to have a very long service time because of the small size of the atrium. The industry expectation is that depleted implantable leadless pacemakers will need to be deactivated and abandoned because of the risks involved in removing chronic implants from the heart. While this may become inevitable, it should be avoided for as long as possible with a device implanted in the atrium because it may not be possible to fit a replacement device into the same atrial chamber as the abandoned depleted implantable device. By relieving the implantable atrial device from the burden of having a CPU and/or pacemaker timer circuit, the implantable atrial device can be made smaller and it will consume less of the battery capacity in a given time, increasing the service time available.

Furthermore, according to an embodiment of the medical system, the first implantable device is configured to detect a cardiac event in the atrium (e.g. atrial contraction) and to transmit through its communication unit a corresponding ultrasonic signal (also denoted as sense marker) to the second implantable device, which ultrasonic signal is indicative of the detected cardiac event.

Further, according to an embodiment of the medical system, the second implantable device is configured to transmit an ultrasonic command signal to the first implantable device, wherein the first implantable device is configured to generate and apply a pacing pulse to the atrium when receiving the ultrasonic command signal.

Further, according to an embodiment of the medical system, the second implantable device comprises an antenna (e.g. an electromagnetic coil) for receiving a programming signal from an external programming device of the medical system, wherein the first implantable device is configured to be programmed via the second implantable device. For example, the second implantable device can be configured to forward a programming signal generated by the programming device or a part of the programming signal in form of an ultrasonic programming signal to the first implantable device.

Since the first implantable device can be configured by the ventricular device, the first implantable device does not require the relatively large coil that is required to allow for inductive communication with an external programming device. Particularly, according to an embodiment, the second implantable device comprises a pacemaker timer for the whole medical system and can be configured to use events reported from other devices such as the first implantable device.

Furthermore, according to an embodiment of the medical system, the medical system comprises a third implantable device that is configured to transmit an ultrasonic signal to the first and/or the second implantable device, and/or that is configured to receive an ultrasonic signal from the first and/or from the second implantable device. Such a third implantable device (e.g. in the form of a subcutaneous device) can be used, for example, to provide capture confirmation when a pace occurs as inputs to the pacemaker timer.

Even with only two implantable devices in a medical (e.g. cardiac) system, communication collisions are possible unless a protocol explicitly avoids the timing where this can occur. Particularly, in an embodiment of a medical system, the system comprises more than two implantable devices. For example, a subcutaneous device may be used to monitor conditions in a body area network and to provide the possibility for RF (RF—radio frequency) based communications from deep implants to a home monitoring system. Also, replacement scenarios are likely to require coordination between devices to ensure proper operation of the replacement device before shutting off the depleted device.

The communications protocol which allows the master/slave coordination messages to be exchanged between the implantable devices must deal with time critical messages, such as sense markers, pace commands and configuration synchronization commands, and also with less time critical message such as the ones used to interrogate statistics from the devices and to configure them. The time critical messages must be sent as circumstances dictate. Preventing collisions of time critical messages is thus inherently more difficult. Analysis of the time critical messages required in a simple pacemaker system reveals that only one particular convergence of events is likely to result in such a collision.

This case is where the pacemaker timer determines that an atrial pace should be delivered at the same instant that an intrinsic atrial sense occurs. In this case, the pacemaker timer will be reset in the same way whether the event was a pace or a sense, and delivering an atrial pace concurrent with an intrinsic cardiac depolarization will have no effect on the heart, so the pacemaker system will be in a safe and appropriate state whether or not either of the messages is successfully delivered to the other implant. When two ultrasound messages are transmitted by different implants at the same time, the most likely outcome is that neither message will be received properly. Loss of one of the non-time-critical messages would potentially result in a less appropriate state for the system, e.g. a configuration change could be ignored or a statistic item could go unreported. Therefore, according to an embodiment the time-critical atrial events are used as a time reference to allow prioritization of other messages between implantable devices of the medical/pacemaker system.

Furthermore, according to an embodiment of the medical system, every cardiac cycle the first implantable device is configured to either apply a pacing pulse to the atrium or to sense an (atrial) cardiac event. The first implantable device is configured to transmit a broadcast message to at least the second implantable device (or to all other implantable device in the medical system) in the form of an ultrasonic signal using the communication unit of the first implantable device after passing of a pre-defined time period after said cardiac event or pacing pulse. The broadcast message indicates whether a cardiac event or a pacing pulse has occurred.

Particularly, the pre-defined period of time can be in the range from 5 ms to 90 ms particularly 5 ms to 50 ms, and preferably 5 ms to 20 ms. A period of 5 ms to 20 ms allows too wait long enough for any disturbances from the event to be over, but also leave as much of the refractory period available to fit messages in.

Furthermore, according to an embodiment of the medical system, the respective implantable device is configured to start a timer when it receives a broadcast message indicating an occurrence of a cardiac event or a pacing pulse has occurred. The timer of each implantable device is configured to let a time duration pass before ending with a timeout, wherein the respective time duration is a unique time duration that differs from the time durations of the other implantable device(s) of the system.

Particularly, according to an embodiment, every message generated by the respective implantable device comprises an address identifier indicating to which target (e.g. first or second implantable device) the message is being sent to. Particularly, one of the address identifiers is a broadcast address identifier that indicates that the respective message is being sent to all devices of the system (e.g. to the second and particularly third implantable device).

Furthermore, according to an embodiment, the time duration of the timer of the respective implantable device depends on the address identifier of the implantable device. Particularly, the shorter the time duration, the higher the implantable device's priority in being able to send a message.

Further, particularly, the communication unit (e.g. a message decoder thereof) in each implantable device of the system is configured to decode all messages at least until the address identifier has been determined. If the respective communication unit (particularly decoder) determines that it is the target for the message, i.e. that the received address identifier matches its own predetermined address identifier, the rest of the message is decoded as well. Particularly, a message targeted to the broadcast address will be fully decoded by all implantable devices in the system.

Furthermore, according to an embodiment of the medical system, the respective implantable device comprises a control unit that is configured to schedule transmission of a message through the communication unit of the respective implantable device, and wherein the respective implantable device is configured to store the message to be sent as a pending message in its communication unit and to set a flag indicating a pending message.

Further, according to an embodiment of the medical system, the communication unit of the respective implantable device is configured to determine at a timeout of the timer of the implantable device whether a receiving circuit of the implantable device is in the process of receiving an incoming message. Wherein in case it is in the process of receiving a message, no message will be sent by the communication unit at least until the next timeout, and wherein in case no message is being received and said flag is set, the communication unit is configured to send the pending message. While it is being transmitted, this message will effectively inhibit the sending of lower priority non-time-critical messages by other implants.

A further aspect of the present invention relates to a medical system, comprising at least a first implantable device and a second implantable device. Each implantable device comprises a communication unit configured to transmit a message (e.g. in form of a modulated ultrasonic pressure wave) to the communication unit of the other implantable device. The first implantable device is configured to periodically transmit a broadcast message to at least the second implantable device (particularly to all implantable devices of the system) using the communication unit of the first implantable device. The broadcast message indicates that an event has occurred, and wherein the first implantable device is configured to transmit the broadcast message after passing of a pre-defined time period after the event, and wherein the respective implantable device is configured to start a timer when it receives a broadcast message indicating an occurrence of an event. The timer of each implantable device is configured to let a time duration pass before ending with a timeout, wherein the respective time duration is a unique time duration that differs from the time durations given to the other devices of the medical system.

As described above, according to an embodiment, the first implantable device can be a first implantable leadless pacemaker that is configured to be implanted into an atrium (e.g. right atrium) of the heart of a patient, and wherein the second implantable device can be a second implantable leadless pacemaker that is configured to be implanted into a ventricle (e.g. on the same side as said atrium, e.g. right ventricle) of the heart of the patient. Particularly, the event can either be an (atrial) cardiac event detected by the first implantable device or a pacing pulse applied to the atrium by the first implantable device. Furthermore, particularly, the pre-defined period of time can take the values already stated above.

Particularly, according to an embodiment, also here every message generated by the communication unit of the respective implantable device can comprise an address identifier indicating to which target (e.g., first or second implantable device) the message is being sent to. Particularly, one of the address identifiers is a broadcast address identifier that indicates that the respective message is being sent to all implantable devices of the system (e.g. to the second and particularly third implantable device).

Furthermore, according to an embodiment, also here, the time duration of the timer of the respective implantable device can depend on the address identifier of the implantable device. Particularly, as explained above, the shorter the time duration, the higher the implantable device's priority in being able to send a message.

Further, particularly, the communication unit (e.g. a message decoder thereof) in each implantable device of the system is configured to decode all messages at least until the address identifier has been determined. If the respective communication unit (particularly decoder) determines that it is the target for the message, i.e. that the received address identifier matches its own predetermined address identifier, the rest of the message is decoded as well. Particularly, a message targeted to the broadcast address will be fully decoded by all implantable devices in the system.

Furthermore, according to an embodiment of the medical system, the respective implantable device comprises a control unit that is configured to schedule transmission of a message through the communication unit of the implantable device. The respective implantable device is configured to store the message to be sent as a pending message in its communication unit and to set a flag indicating a pending message.

Furthermore, according to an embodiment of the medical system, the communication unit of the respective implantable device is configured to determine at a timeout of the timer of the respective implantable device whether the receiving circuit of the respective implantable device is in the process of receiving an incoming message, wherein in case it is in the process of receiving a message, no message will be sent by the communication unit at least until the next timeout, and wherein in case no message is being received and the flag is set, the communication unit is configured to send the pending message.

Other features which are considered as characteristic for the invention are set forth in the appended claims.

Although the invention is illustrated and described herein as embodied in intra-cardiac communications using ultrasound to provide direct timing information without electrical interferences, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 2 is a schematical illustration of a first embodiment of an intracardiac pacing device; and FIG. 3 is a schematical illustration of a second embodiment of the intracardiac pacing device.

DETAILED DESCRIPTION OF THE INVENTION

Figure 1:
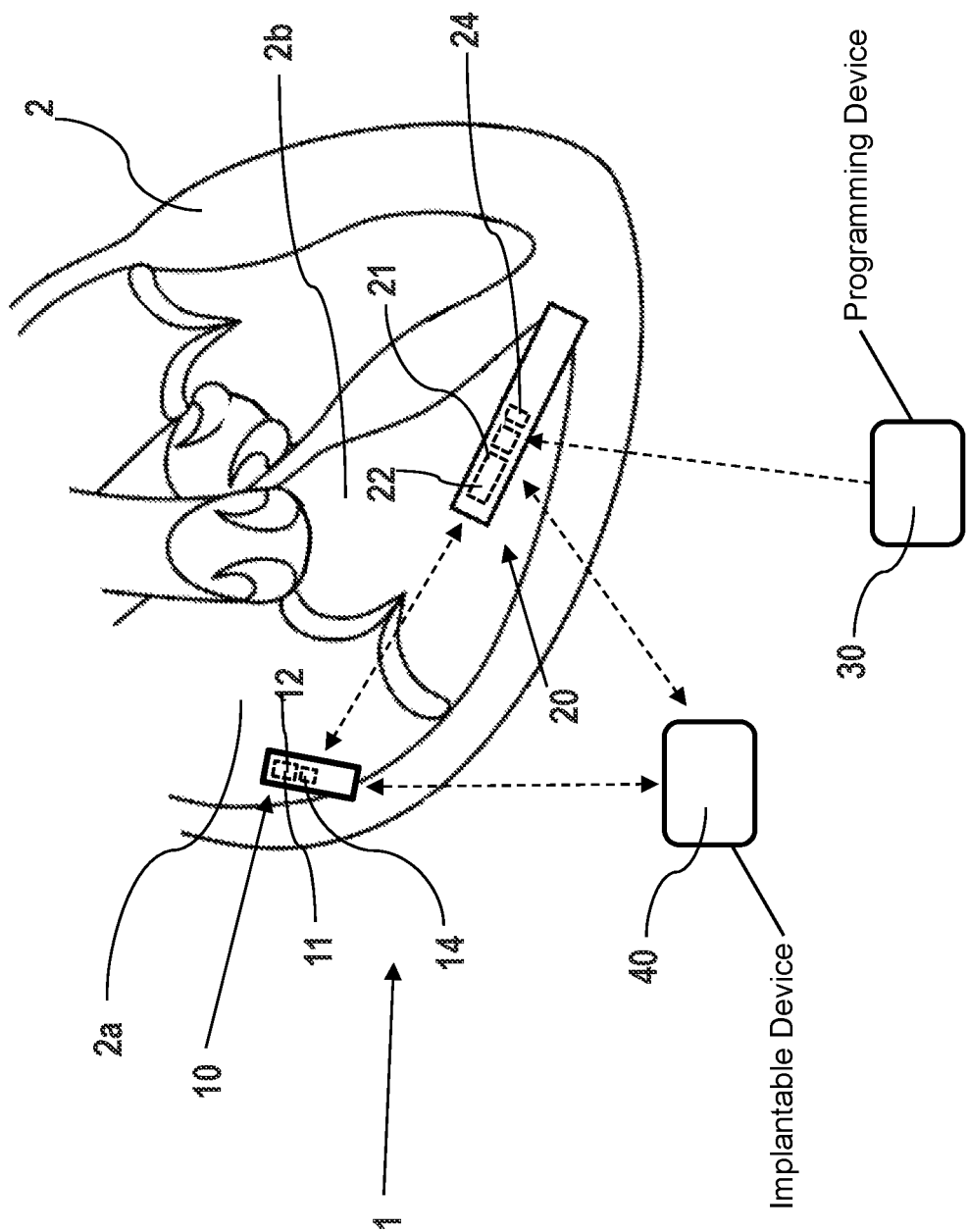
FIG. 1 is a schematical illustration of an embodiment of a medical system according to the invention.

Referring now to the figures of the drawings in detail and first, particularly to FIG. 1 thereof, there is shown an embodiment of a medical system 1 comprising a first implantable device 10 and a second implantable device 20, wherein each implantable device 10, 20 comprises a communication unit 11, 21 configured to transmit an ultrasonic signal to the communication unit 21, 11 of another implantable device 20, 10 of the medical system 1.

Here, as an example, the first and the second implantable devices 10, 20 are formed by implantable leadless pacemakers 10, 20, wherein the first implantable leadless pacemaker 10 is implanted in an atrium (e.g. right atrium) 2a of the heart 2 of a patient, and wherein the second implantable leadless pacemaker 20 is implanted in the ventricle 2b of the heart 2. Concerning cardiac pacing of the heart 2, particularly maintaining atrioventricular (AV) synchrony is of high importance. AV synchrony means that in the (normal) activation sequence of the heart the atria contract first and then, after an appropriate delay, which is denoted as atrioventricular (AV) delay, the ventricles contract. When the timing between the two chambers goes out of synchronization, less blood is delivered on each beat and the cardiovascular output decreases. Thus, an appropriate communication should be achieved between the devices 10, 20 in order to be able to provide proper pacing.

For this, each chamber 2a, 2b of the heart 2 which needs to be paced preferably gets a leadless pacemaker 10, 20 that is capable of sensing cardiac events within that chamber (e.g. atrial contraction or ventricular contraction, respectively) and of pacing the heart in that chamber 2a, 2b. According to an embodiment, each device 10, 20 gets a piezoelectric transducer 12, 22 which allows transmission of a modulated ultrasonic pressure wave that can propagate through the cardiac tissue to the devices 10, 20 in the other chamber 2a, 2b. Particularly, the same transducer 11, 12 can also convert received modulated pressure waves into electrical signals which can be demodulated to restore the originally transmitted signal.

Particularly, according to an embodiment, the communication unit 11, 21 of the respective device 10, 20 comprises a hardware-based state machine to implement a protocol where the messages are either sent immediately for time-sensitive messages or are delayed until a particular timeslot for non-time-sensitive messages.

Even with only two implantable devices 10, 20 in the system 1, communication collisions are possible unless the protocol explicitly avoids the timing where this can occur. Preferably, in an embodiment, the system 1 can also include more than two implantable devices 10, 20. For example, as also indicated in FIG. 1, a subcutaneous device (third implantable device) 40 may be used to monitor conditions in a body area network and to provide the possibility of radio frequency-based communications from deep implants to a home monitoring system.

Particularly, in a medical system 1 such as a pacemaker system comprising the first and second implantable leadless pacemaker 10, 20 as shown in FIG. 1, time critical messages can be the atrial sense markers (i.e. a message indicating an atrial cardiac event) that are preferably broadcasted from the first device to all other devices 20 in the system 1; messages relating to "Sync After Pace", which are preferably sent from the first device 10 to all other devices 20 in the system; messages relating to "Sync After Sense", which are preferably sent from the first device 10 to all other devices 20 in the system, the command messages or signals sent from the second device 20 to the first device 10 and forcing the first device 10 to apply a pacing pulse to the atrium 2a; messages relating to "Do Cross Channel Blanking" that are sent from the second device 20 to the first device 10. "Sync after Pace" indicates that a pacing pulse has occurred. "Sync after Sense" indicates that a cardiac event occurred. Thus, the broadcast message indicates whether a cardiac event or a pacing pulse has occurred. If the pacemaker in one chamber is going to pace, the sense detection circuit in the other chamber should be blanked (inhibited from detecting) during the time of the pace in order to avoid a false sense from being detected due to the effects of pacing in the other chamber. The blanking period can be pre-defined, so only the start of this blanking period needs to be communicated to the chamber which is not about to pace. This is done by the message "Do Cross Channel Blanking". This is a time-critical message because it tells the receiving device when (starting now) it needs to do something.

On the other hand, non-time-critical messages that require a lower priority may relate to messages sent from the second device to the first device to initiate one of: Write to Register, Read from Register, Activate Program on next sync, Disable Permanently, or may relate to messages sent from the first device to the second device to initiate e.g.: Read from Register Response. Registers are memory locations in the device that configure how it should behave. Writing to a register is done to change a configuration. Reading a register is used to tell how a device was previously configured. Registers can also be used to pass status information about something that happened. Activate Program is used to tell the device that it should use a pre-defined collection of registers to change its own configuration at some particular point of time, particularly at some point of the next cardiac interval. Disable Permanently is a command for the device to shut itself off completely and permanently because it is being replaced by a new device. When a message requests some information from another device (i.e. a Read from Register command), the addressed device sends a response message. The message identifies that it is a response to a previous request.

Preferably, every cardiac cycle, the first device 10 in the atrium 2a either paces or detects an atrial intrinsic sense (cardiac event in the atrium 2a). After a fixed time period from this event that can be of the order of 10 ms for example, the atrial device 10 sends a broadcast message indicating that it has either paced or sensed. This message becomes the reference point for the non-time-critical message time slots.

For this, the respective implantable device 10, 20 is preferably configured to start a timer when it receives a broadcast message indicating an occurrence of a cardiac event or a pacing pulse has occurred, wherein the timer of each implantable device 10, 20 is configured to let a time duration pass before ending with a timeout. The respective time duration is a unique time duration that differs from the time durations of the other implantable device(s) 20, 10 of the system 1.

Particularly, every message generated by the respective implantable device 10, 20 comprises an address identifier indicating to which target (e.g. first or second implantable device 10, 20) the message is being sent to. Particularly, one of the address identifiers is a broadcast address identifier that indicates that the respective message is being sent to all devices of the system (e.g. to the second implantable device 20).

Particularly, the time duration of the timer of the respective implantable device 10, 20 depends on the address identifier of the respective implantable device 10, 20. The shorter the time duration, the higher the implantable device's 10, 20 priority in being able to send a message.

Further, particularly, the communication unit (e.g. a message decoder thereof) 11, 21 in each implantable device 10, 20 of the system 1 is configured to decode all messages at least until the address identifier has been determined. If the respective communication unit (particularly decoder) 11, 21 determines that it is the target for the message, i.e. that the received address identifier matches its own predetermined address identifier, the rest of the message is decoded as well. Particularly, a message targeted to the broadcast address will be fully decoded by all implantable devices 10, 20 of the medical system 1.

Particularly, as indicated in FIG. 1, the respective implantable device 10, 20 preferably comprises a control unit 14, 24 that is configured to schedule transmission of a message through the communication unit 11, 21 of the respective implantable device 10, 20, and wherein the respective implantable device 10, 20 is configured to store the message to be sent as a pending message in its communication unit 11, 21 and to set a flag indicating a pending message. Further, the communication unit 11, 21 of the respective implantable device 10, 20 is configured to determine at a timeout of the timer of the corresponding implantable device 10, 20 whether a receiving circuit of the respective implantable device 10, 20 is in the process of receiving an incoming message. In case it is in the process of receiving a message, no message will be sent by the respective communication unit 11, 21 at least until the next timeout, and wherein in case no message is being received and the flag is set, the corresponding communication unit 11, 21 is configured to send the pending message. While it is being transmitted, this message will effectively inhibit the sending of lower priority non-time-critical messages by other implants. Particularly, when two ultrasonic messages are transmitted by different implantable device of the system 1 at the same time, the most likely outcome is that neither message will be received properly. Only time where collision of time-critical messages is likely is tolerant of all possible communications results. Time-critical messages must be sent at same time where an event occurred or where an event is being triggered. It is possible that the system may try to trigger an atrial pace at the same time as an atrial sense occurs. In this case, the trigger message and the sense detection message may corrupt each other, but the system will be in an appropriate state whether one or the other or both messages are not properly received. No other concurrent time critical message pairs are expected.

In other words, each implantable device 10, 20 has a unique predetermined delay (time duration of the corresponding timer) after which it can start sending a queued message. The state machine of the communication unit 11, 21 that handles sending messages always checks for whether the ultrasound carrier frequency is present before starting a transmission. Every message packet always starts with an active start bit. This protocol inhibits the starting of a message when an active message is already in progress. Device priorities result from whichever device 10, 20 has the shortest delay (i.e. time duration of the respective timer) after the timeslot reference point indicated by the respective broadcast message relating to the atrial pacing event or detected atrial cardiac event.

Preferably, the packet definition for the protocol includes bits which indicate the address of the message recipient. One address is reserved to indicate that the message is broadcast to all listeners. The receiving state machine of the respective communication unit 11, 21 detects whether an incoming message is targeted at this device and only processes messages that it is supposed to receive. Preferable, the addresses are configurable to allow robust replacement of a nearly depleted device 10, 20 with a new one. The old device address would be changed to one different than the factory delivered addresses so that a new factory delivered device can be controlled in the system 1 separately until it has passed clinical testing. At that point, the old device can be deactivated concurrent with fully enabling the new device.

The medical system 1 shown in FIG. 1 is simplified by having a single pacemaker timer sub-system in the second device 20. This pacemaker timer can command paces in other devices (e.g. in the first device 10) using a targeted pace command (a time-sensitive message). Sensing in other devices 10 can be conveyed to the second device 20 with the pacemaker timer using sense flag broadcast messages (also a time-sensitive message).

If electrical noise interferes with sense detection in a normal pacemaker, the pacemaker goes into noise mode. In this mode, no senses can be reliably detected, so the pacemaker paces asynchronously to ensure that cardiac support is provided whether or not there is suitable intrinsic cardiac activity. Some pacemaker features change their behavior when noise mode is active. This kind of information can be shared between leadless devices in all chambers using "Start Noise" and "End Noise" broadcast markers.

Furthermore, one device 10, 20 can send configuration messages to another device 20, 10 in the form of Write commands to particular registers in the destination device (see above). These registers can use double buffering to delay the activation of the new configuration until a Transfer Registers command is sent to cause all registers to change to the new configuration at the same time. The Write command is a non-time-sensitive command. The Transfer Registers command can be a time-sensitive command to support configuration changes with intrinsic cardiac timing.

The present invention avoids the need for far field sensing from another chamber in a multiple device medical system such as a leadless pacemaker system. Due to the ultrasound communication, the occupied space of the atrial device can be reduced. This is due to the fact that the atrial device can be relieved from the burden of having a CPU and/or pacemaker timer circuit which also reduces the necessary battery capacity in a given time period. Since the atrial device 10 can be configured by the ventricular device 20 (which can use simultaneous inductive communications to an external programming device 30), the atrial device 10 does not require the relatively large coil that is required to allow for inductive communications with an external programming device 30. Particularly, the ventricular device 20 can contain the pacemaker timer for the whole system 1 and can use events reported from other devices such as the atrial device 10 as inputs to the timing logic. Further, also a subcutaneous implantable third device 40 can be used (cf. FIG. 1) to provide capture confirmation when a pace occurs. Furthermore, the invention allows a robust replacement scheme of depleted devices. Finally, the present invention provides a general mechanism for exchanging information between devices without collisions or interference from the electrical signals resulting from cardiac events.

FIG. 2 shows a schematic illustration of an intracardiac pacing device (also called implantable leadless pacemaker). The device comprises a housing 100 which surrounds an energy storage 102 (e.g. a battery), an electronic module 103, a first communication unit 104, and a second communication unit 107. The housing 100 may comprise titanium or may be made of titanium.

At a distal end of the housing 100, a first electrode 106 (also called pacing/sensing electrode) is disposed. In a proximal region of the housing 100, a second electrode 101 (also called return electrode) is arranged. The second electrode 101 may be formed as a ring electrode.

The device may be fixed to cardiac tissue by a fixation element 105. The fixation element may be formed as a tine. It may comprise Nitinol or may be made of Nitinol. In one embodiment, four tines 105 made of Nitinol may be formed at the distal end of the housing 100.

The energy storage 102 may be configured to provide electrical energy to the components of the device, in particular to the electronic module 103, the first communication unit 104, the second communication unit 107, and the first electrode 106.

The electronic module 103 may be configured to perform the functions of a pacemaker, including sensing cardiac events and providing pacing pulses. The electronic module 103 may comprises a processor and memory and/or state machine logic.

The first communication unit 104 may be configured for communication with an external device (e.g. a programmer). The first communication unit may be formed as a coil for inductive communication.

The second communication unit 107 may be configured for transmitting and/or receiving ultrasonic waves. It may be a piezoelectric transducer.

FIG. 3 shows another embodiment of another intracardiac pacing device which has the same components as in FIG. 2 without the first communication unit. Thus, the other device can only communicate via ultrasound. By omitting the first communication unit, the other device may have a smaller form factor than the device according to FIG. 2.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. A medical system, comprising:
   implantable devices including at least a first implantable device and a second implantable device, wherein each of said implantable devices having a communication unit configured to transmit an ultrasonic signal to said communication unit of another one of said implantable devices of the medical system;
   wherein for every cardiac cycle said first implantable device is configured to either apply a pacing pulse to an atrium or to sense a cardiac event;
   wherein said first implantable device is configured to transmit a broadcast message to at least said second implantable device in a form of the ultrasonic signal using said communication unit of said first implantable device after a passing of a pre-defined time period after the cardiac event or the pacing pulse;
   wherein the broadcast message indicates whether the cardiac event or the pacing pulse has occurred in the atrium;
   wherein each of said implantable devices has a timer and is configured to start said timer upon receiving the broadcast message indicating an occurrence of the cardiac event or the pacing pulse;
   wherein said timer of said implantable devices is configured to let a time duration pass before ending with a timeout; and
   wherein the time duration is a unique time duration that differs from the time duration which passes before ending with a timeout in all other ones of said implantable devices.

2. The medical system according to claim 1, wherein said communication unit has a piezoelectric transducer.

3. The medical system according to claim 1, wherein said communication unit is configured to receive the ultrasonic signal from said communication unit of another one of said implantable devices of the medical system.

4. The medical system according to claim 1, wherein:
   said first implantable device is a first implantable leadless pacemaker that is configured to be implanted into an atrium of a heart of a patient; and
   said second implantable device is a second implantable leadless pacemaker that is configured to be implanted into a ventricle of the heart of the patient.

5. The medical system according to claim 4, wherein said first implantable device is configured to detect a cardiac event in the atrium and to transmit through said communication unit a corresponding ultrasonic signal to said second implantable device, the corresponding ultrasonic signal being indicative of a detected cardiac event.

6. The medical system according to claim 4, wherein:
   said second implantable device is configured to transmit an ultrasonic command signal to said first implantable device; and
   said first implantable device is configured to generate and apply a pacing pulse to the atrium when receiving the ultrasonic command signal.

7. The medical system according to claim 1, wherein:
said second implantable device has an antenna for receiving a programming signal from an external programming device; and
said first implantable device is configured to be programmed via said communication unit of said second implantable device.

8. The medical system according to claim 1, further comprising a third implantable device that is configured to transmit an ultrasonic signal to said first implantable device and/or said second implantable device, and/or that is configured to receive the ultrasonic signal from said first implantable device and/or from said second implantable device.

9. The medical system according to claim 1, wherein:
said implantable devices each having a controller that is configured to schedule a transmission of a message through said communication unit of a respective one of said implantable devices; and
said implantable devices are each configured to store the message to be sent as a pending message in said communication unit and to set a flag indicating the pending message.

10. The medical system according to claim 1, wherein:
said communication unit has a receiver; and
said communication unit of a respective one of said implantable devices is configured to determine at the timeout of said timer of said respective implantable device whether said receiver of said communication unit of said respective implantable device is in a process of receiving an incoming message, wherein in a case where said respective implantable device is in the process of receiving the message, no message will be sent by said communication unit at least until a next timeout, and wherein in case no message is being received a flag is set, and said communication unit is configured to send a pending message.

11. A medical system, comprising:
implantable devices including at least a first implantable device and a second implantable device, wherein each of said implantable devices having a timer and a communication unit configured to transmit a message to said communication unit of another one of said implantable devices of the medical system, wherein said first implantable device is configured to periodically transmit a broadcast message to at least said second implantable device using said communication unit of said first implantable device, wherein the broadcast message indicates that an event has occurred, and wherein said first implantable device is configured to transmit the broadcast message after passing of a pre-defined time period after the event, and wherein a respective one of said implantable devices is configured to start said timer when it receives the broadcast message indicating an occurrence of the event, wherein said timer of each of said implantable devices is configured to let a time duration pass before ending with a timeout, wherein the time duration of each of said implantable devices is a unique time duration that differs from the time duration which passes before ending with a timeout in all other ones of said implantable devices.

12. The medical system according to claim 11, wherein:
said respective implantable device has a controller that is configured to schedule a transmission of the message through said communication unit of said respective implantable device; and
said respective implantable device is configured to store the message to be sent as a pending message in said communication unit and to set a flag indicating the pending message.

13. The medical system according to claim 11, wherein said communication unit of said respective implantable device is configured to determine at a timeout of said timer of said respective implantable device whether a receiver of said communication unit of said respective implantable device is in a process of receiving an incoming message, wherein in case said receiver is in the process of receiving the incoming message, no message will be sent by said communication unit at least until a next timeout, and wherein in case no message is being received a flag is set, and said communication unit is configured to send a pending message.

* * * * *